United States Patent [19]

Li

[11] 4,250,087

[45] Feb. 10, 1981

[54] CARBOXYL TERMINUS ANALOGS OF β-ENDORPHIN

[75] Inventor: Choh H. Li, Berkeley, Calif.

[73] Assignee: Hoffmann-La Roche Inc., Nutley, N.J.

[21] Appl. No.: 102,094

[22] Filed: Dec. 10, 1979

Related U.S. Application Data

[63] Continuation-in-part of Ser. No. 47,200, Jun. 11, 1979, abandoned.

[51] Int. Cl.³ .......................................... C07C 103/52
[52] U.S. Cl. ................................................ 260/112.5 R
[58] Field of Search ................ 260/112.5 R; 424/177

[56] References Cited

U.S. PATENT DOCUMENTS

| | | | |
|---|---|---|---|
| 4,038,222 | 7/1977 | Li | 424/177 |
| 4,116,950 | 9/1978 | Li | 424/177 |

*Primary Examiner*—Delbert R. Phillips
*Attorney, Agent, or Firm*—Jon S. Saxe; George M. Gould; John B. Wilson

[57] ABSTRACT

Novel carboxyl terminus analogs of β-endorphin are described. The carboxyl terminus of such analogs is selected from lower alkyl amide, glycine, glycinamide, or polyglycine. These analogs exhibit either greater analgesic activity than the parent β-endorphin and/or increased binding activity in an opiate binding assay.

11 Claims, No Drawings

CARBOXYL TERMINUS ANALOGS OF β-ENDORPHIN

RELATED APPLICATIONS

This application is a continuation-in-part of copending U.S. Application Ser. No. 47,200, filed June 11, 1979, now abandoned.

BACKGROUND OF THE INVENTION

U.S. Pat. No. 4,038,222, issued July 26, 1977 and subsequently reissued as U.S. Pat. No. Re. 29,842 on Nov. 21, 1978 describes the isolation, characterization, synthesis and pharmacological activity of human, porcine and ovine β-endorphin.

U.S. Pat. No. 4,116,950, issued Sept. 26, 1978 describes a series of human β-endorphin analogs which are modified in the carboxyl terminus region with phenylalanine in position 27 and glycine in position 31 and optionally with further substitutions in the amine terminus region such as D-threonine in position 2, or norleucine in position 5 or alanine in positions 6 and 7.

Of all the opioid peptides that correspond to a portion of the structure of β-lipotropin only the structure corresponding to positions 61–91, namely β-endorphin (β-Ep), has shown potent analgesic activity by the intravenous route. Recent studies with synthetic analogs indicate that the complete primary structure of β-endorphin is required for full analgesic activity. See Li et al., Biochem. Biophys. Res. Commun. 85, 795 (1978). Although modifications of the pentapeptide met-enkephalin, representing positions 1 to 5 of β-endorphin, can lead to products with potencies comparable to or even greater than that of β-endorphin, efforts to make the same modifications in positions 1 to 5 of β-encorphin have not led to analogs with increased potencies. Thus far the only analog of β-endorphin that has exhibited greater analgesic activity than the parent is [Phe$^{27}$, Gly$^{31}$]-$\beta_h$-EP whose potency is about 1.48 times that of the parent by the intravenous assay route. Note U.S. Pat. No. 4,116,950 above. It has now been found that modifications in position 31 and extension at this terminus can unexpectedly lead to compounds exhibiting greater biological potencies.

DESCRIPTION OF THE INVENTION

The present invention relates to analogs of β-endorphin as represented by the following formula:

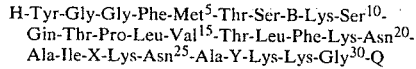

wherein B is Glu or Gln; X is Ile or Val; Y is His or Tyr and Q is —NH—lower alkyl or (Gly)$_n$—A where n is an integer from 1 to 5 and A is —OH or —NH$_2$.

Compounds of Formula I where X is Ile and Y is His correspond to camel (also known as ovine) β-endorphin ($\beta_c$-EP) analogs. Correspondingly compounds of Formula I where X is Val and Y is His correspond to porcine β-endorphin ($\beta_p$-EP) analogs. Additionally, compounds of formula I where X is Ile and Y is Tyr correspond to human β-endorphin ($\beta_h$-EP) analogs.

Preferred compounds of Formula I are obtained when X is Ile and Y is Tyr and when n is 1 and A is —OH, i.e., [Gly$^{31}$]-$\beta_h$-EP; n is 1 and A is —NH$_2$, i.e., [Gly$^{31}$]-$\beta_h$-endorphinamide, n is 2 and A is —OH, i.e, [Gly$^{31}$]-$\beta_h$ endorphinyl glycine, n is 2 and A is —NH$_2$, i.e., [Gly$^{31}$]-$\beta_h$-EP-Gly-NH$_2$ and n is 3 and A is —NH$_2$, i.e., [Gly$^{31}$]-$\beta_h$-EP-Gly-Gly-NH$_2$. A most preferred compound of the invention is obtained when B is Gln, n is 3 and A is —NH$_2$ i.e., [Gln$^8$, Gly$^{31}$]-$\beta_h$-EP-Gly-Gly-NH$_2$.

The term lower alkyl as used herein is meant to include straight or branched chain alkyl groups having one to seven carbon atoms, preferably four to six carbon atoms. A most preferred alkyl group is n-amyl.

The compounds of the invention can be conveniently prepared by utilizing peptide synthesis procedures well known in the art. Preferred procedures useful in preparing the instant compounds involve the solid phase method of Merrifield, J. Am. Chem. Soc. 85, 2149 (1963) as performed on Boc-Gly polymer or brominated polymer (see U.S. Pat. No. 4,116,950 or Li et al., J. Med. Chem. 20, 325 (1977)) for analogs with COOH-terminal glycine residues and on Boc-Gly benzhydrylamine polymer (see Pietta and Marshall, J. Chem. Soc. D, 650 (1970)) for analogs with a COOH-terminal glycineamide residue. Procedures used in preparing the $\beta_h$-endorphin sequence are set forth in U.S. Pat. No. 4,116,950 while procedures employed in preparing the $\beta_c$ and $\beta_p$-endorphin sequences have been described in U.S. Pat. No. Re. 29,842. For analogs where n=2 or greater the appropriate, preformed polyglycinyl compound can be introduced as a single entity in analogous manner to the single glycine moiety unto either of the aforesaid polymer systems.

The Boc-glycyl resin is then alternatively subjected to deblocking in 55% trifluoroacetic acid (methylene chloride, neutralizing with diisopropylethylamine and finally coupled with the preformed symmetrical anhydride of the next Boc amino acid in the sequence. After completion of the synthetic cycles with all required amino acids, the final protected peptide resin is treated with liquid HF in a manner known per se to yield the free crude product. Purification is accomplished by chromatography on carboxymethylcellulose followed by partition chromatography on Sephadex G-50 as detailed in Li et al., J. Med. Chem., supra.

For the synthesis of lower alkyl amides, the 3-nitro-4-bromomethylbenzamidomethyl (NBA) linking group is used for establishing a photolabile link between peptide and polymer. This linking group and its use in solid phasepeptide syntheis is described by Rich and Gurwara, J. Am. Chem. Soc. 97, 1575–1579 (1975).

Characterization of the final product peptides is accomplished by amino acid analysis of acid hydrolysates and enzyme digests, paper electrophoresis and thin layer chromatography.

The compounds of the present invention are potent opiate agonists and thus are useful as analgesics, narcotic antagonists and anti-diarrhea agents.

They can be used as medicaments in the form of pharmaceutical preparations having direct or delayed liberation of the active ingredient which contain them in association with a compatible carrier material. This carrier material can be an organic or inorganic inert carrier material suitable for enternal, precutaneous or parenteral application such as water, gelatin, gum arabic, lactose, starch, magnesium stearate, talc, vegetable oils, polyalkylene-glycols, petroleum jelly, etc. The pharmaceutical preparations can be made up in a solid form (e.g., as tablets, dragees, suppositories or capsules) or in a liquid form (e.g., as solutions, suspensions or emulsions). A preferred form suitable for parenteral administration involves preparation of a purified, lyophilized form of the active compound which is reconstituted prior to use by the addition of sterile, distilled water or saline.

If necessary, the pharmaceutical preparations can be sterilized and/or contain adjuvant substances such as preserving, stabilizing, wetting or emulsifying agents, salts for the variation of the osmotic pressure or substances acting as buffers.

The compounds of the present invention can be conveniently administered by the parenteral route preferably intravenously with a dosage in the range of about 1 mg. to 50 mg. per administration.

Also equivalent to the aforesaid β-endorphin analogs for the purposes of this invention are the pharmaceutically acceptable acid additiona salts thereof. Such acid addition salts can be derived from a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicylic, gluconic, ascorbic and related acids.

The following Examples serve to further illustrate the present invention.

EXAMPLE 1

Synthesis

Solid phase synthesis was performed on Boc-Gly polymer or brominated polymer for analogs with COOH-terminal glycine residues and on Boc-Gly benzhydrylamine polymer for the analog with a COOH-terminal glycineamide residue. Side-chain protection and coupling were performed as described previously for the synthesis of human β-endorphin as described in U.S. Pat. No. 4,116,950. Assembly of sequences corresponding to [Gly$^{31}$]-$\beta_h$-EP (I), [Gly$^{31}$]-$\beta_h$-endorphinamide i.e., ([Gly$^{31}$]-$\beta_h$-EP-NH$_2$) (II), and [Gly$^{31}$]-$\beta_h$-endorphinylglycine i.e., ([Gly$^{31}$]-$\beta_h$-EP-Gly-OH) (III) was carried out in a Beckman model 990 peptide synthesizer with the symmetrical anhydride program fully automated. After removal of the last Boc group with trifluoroacetic acid and treatment with liquid HF, the peptides were purified by gel filtration on Sephadex G-10 and chromatography on carboxymethylcellulose by procedures detailed previously in U.S. Pat. No. 4,116,950. Final purification by differential hydrophobicity was effected by partition chromatography on Sephadex G-50 with solvent systems used and $R_f$ values obtained as follows: I, 1-butanol:pyridine:0.05 M NH$_4$OAc-0.2% HOAc (5:3:10), $R_f$ 0.39; II, 1-butanol:HOAc:Pyridine:H$_2$O (20:5:1:25), $R_f$ 0.37; III, 1-butanol:pyridine:0.6 M NH$_4$OAc (5:3:10), $R_f$ 0.61. From 50 umol of starting Boc-Gly resin there was obtained: I, 65.8 mg; II, 62.2 mg; III, 67.3 mg. The peptides were homogeneous in tlc (silica gel with ninhydrin and Cl$_2$-tolidine detection) in 1-butanol:pyridine:acetic acid:H$_2$O (5:5:1:4), as follows: I, $R_f$ 0.47; II, $R_f$ 0.50; III, $R_f$ 0.52. They were homogeneous on paper electrophoresis on Whatman 3MM (400 V, 5 hr, ninhydrin detection) at pH 3.7 (I, $R_f$ 0.57; II, $R_f$ 0.65; IV, $R_f$ 0.56) and at pH 6.7 (I, $R_f$ 0.46; II, $R_f$ 0.57; III, $R_f$ 0.46) with $R_f$ values relative to lysine. Amino acid analyses of 24-hr acid hydrolysates were in agreement with expected values (Table 1).

TABLE 1

| Amino Acid Analyses of Synthetic $\beta_h$-EP Analogs[a] | | | |
|---|---|---|---|
| Amino Acid | [Gly$^{31}$]-$\beta_h$-EP | [Gly$^{31}$]-$\beta_h$-EP—NH$_2$ | [Gly$^{31}$]-$\beta_h$-EP—Gly—OH |
| Lys | 4.98 (5) | 5.02 (5) | 4.91 (5) |
| Asp | 1.98 (2) | 2.01 (2) | 2.01 (2) |
| Thr | 2.74 (3) | 2.72 (3) | 2.79 (3) |
| Ser | 1.76 (2) | 1.75 (2) | 1.76 (2) |
| Glu | 2.23 (2) | 2.20 (2) | 2.15 (2) |
| Pro | 1.04 (1) | 1.03 (1) | 1.04 (1) |
| Gly | 3.84 (4) | 3.78 (4) | 4.82 (5) |
| Ala | 2.09 (2) | 2.07 (2) | 2.10 (2) |
| Val | 1.01 (1) | 1.00 (1) | 0.99 (1) |
| Met | 0.98 (1) | 0.95 (1) | 0.98 (1) |
| Ile[b] | 1.39 (2) | 1.44 (2) | 1.37 (2) |
| Leu | 2.08 (2) | 2.05 (2) | 2.09 (2) |
| Tyr | 1.93 (2) | 1.94 (2) | 1.93 (2) |
| Phe | 1.99 (2) | 1.99 (2) | 1.93 (2) |

[a]Run on 24-hr 6 N HCl hydrolysates (theoretical values in parentheses).
[b]Low values are accounted for by the presence of the acid resistant Ile-Ile moiety.

EXAMPLE 2

Biological Activity

Opiate activity was measured from the depression of electrically-stimulated contractions of guinea pig ileum preparations, see Kosterlitz et al., J. Pharmacol. 39, 398 (1970) and Doneen et al., Biochem. Biophys. Res. Commun. 74, 656 (1977). For analgesic assay, male ICR mice weighing 25–30 g (Simonsen Laboratories, Gilroy, CA) were used. Analgesic activity was assessed by the tail-flick method of D'Amour and Smith as described by Li et al., Biochem. Biophys. Res. Commun. 85, 795 (1978).

The opiate receptor binding assay was performed by the method of Pasternak et al., Mol. Pharmacol. 11, 340 (1975) with modifications using a membrane fraction from rat brain homogenate. [$^3$H-Tyr$^{27}$]-$\beta_h$-EP was used as primary ligand and synthetic $\beta_h$-EP as standard competing ligand.

The biological activities of the analogs were measured by in vitro and in vivo procedures.

TABLE 2

| Opiate Activity of Synthetic $\beta_h$-Endorphin Analogs Substituted at Position 31 and Extended at the COOH Terminal | | |
|---|---|---|
| Synthetic peptides | IC$_{50}$[a] (M) | Relative potency |
| $\beta_h$-Endorphin | 12.8 × 10$^{-8}$ | 100 |
| [Gly$^{31}$]-$\beta_h$-EP | 7.6 × 10$^{-8}$ | 168 |
| [Gly$^{31}$]-$\beta_h$-EP—NH$_2$ | 6.4 × 10$^{-8}$ | 200 |
| [Gly$^{31}$]-$\beta_h$-EP—Gly—OH | 9.7 × 10$^{-8}$ | 132 |

[a]Guinea pig ileum assay.

TABLE 3

| Analgesic Potency of Synthetic $\beta_h$-Endorphin Analogs Substituted at Position 31 and Extended at the COOH Terminal | | |
|---|---|---|
| Synthetic peptides | AD$_{50}$[a] | Relative Potency |
| $\beta_h$-Endorphin | 0.064 (0.026–0.17) | 100 |
| [Gly$^{31}$]-$\beta_h$-EP | 0.077 (0.038–0.17) | 83 |
| $\beta_h$-Endorphin | 0.036 (0.019–0.068) | 100 |
| [Gly$^{31}$]-$\beta_h$-EP—NH$_2$ | 0.016 (0.008–0.032) | 225 |
| $\beta_h$-Endorphin | 0.092 (0.061–0.14) | 100 |
| [Gly$^{31}$]-$\beta_h$-EP—Gly—OH | 0.043 (0.031–0.057) | 217 |

[a]AD$_{50}$ in nmole (95% confidence limit) by intracerebroventricular injection.

For comparison, the relative potencies ($\beta_h$-EP=100) previously obtained for [Phe$^{27}$, Gly$^{31}$]-$\beta_h$-EP were 128 in the guinea pig ileum assay and 119 in the in vivo assay used herein. Thus, the double substitutions in positions 27 and 31, which are the two variable residues when camel and human β-endorphins are compared, did not substantially change either activity. However, the single replacement of Glu-31 in $\beta_h$-EP by Gly appears to substantially raise the in vitro activity (Table 2) but not significantly alter the analgesic potency (Table 3). Such results would be consistent with earlier observations that the structural requirements for the two activities differ.

The opiate activities of the synthetic analogs as measured by the rat brain receptor assay are summarized in Table 4. All the analogs exhibit greater potency than $\beta_h$-EP in the receptor and guinea pig ileum assays. Interestingly, the analog with a COOH-terminal carboxamide appears to be the most active. In the receptor assay (Table 4), [Gly$^{31}$]-$\beta_h$-endorphinamide is almost three times more potent in comparison with the parent peptide. Similar increases in activity in the myenteric plexus bioassay have been observed in going from Met-enkephalin to Met-enkephalinamide and from $\beta$-LPH-(61-76) to the amide form. As reported by Ling and Guillemin, Proc. Natl. Acad. Sci. U.S.A. 73, 3308 (1976).

The analgesic potency of $\beta_h$-EP appears to be practically unchanged by the replacement of Glu-31 by Gly, indicating that the side-chain of Glu is not necessary for this activity. Conversion of the COOH-terminal carboxyl group of [Gly$^{31}$]-$\beta_h$-Ep to a carboxamide or extension by an additional Gly residue results in increases in analgesic potency. In view of the fact that the entire chain length of $\beta_h$-EP has been indicated to be required for full analgesic activity, it is evident that even limited enzymatic attack at the COOH-terminus could rapidly destroy its activity. Thus, modification of position 31 and extension at the COOH-terminus may be one approach toward analogs with greater biological activity than $\beta$-endorphin.

TABLE 4

Receptor Binding Assay of Synthetic $\beta_h$-Endorphin analogs Substituted at Position 31 and Extended at the COOH Terminal

| Peptide | IC$_{50}$$^a$ | Relative potency |
|---|---|---|
| $\beta_h$-Endorphin | 0.75 × 10$^{-9}$ | 100 |
| [Gly$^{31}$]-$\beta_h$-EP | 0.59 × 10$^{-9}$ | 127 |
| [Gly$^{31}$]-$\beta_h$-EP—Gly | 0.49 × 10$^{-9}$ | 153 |
| [Gly$^{31}$]-$\beta_h$-EP—NH$_2$ | 0.30 × 10$^{-9}$ | 250 |

$^a$50% inhibiting concentration in M (see FIG. 2) in the opiate receptor binding assay.

EXAMPLE 3

Materials

Chloromethylated-1%-polymer (0.74 mmole/g.) was obtained from Lab Systems. Benzhydrylamine-1%-polymer was obtained from Beckman. 3-Nitro-4-bromomethylbenzoic acid was prepared by the method of Rich and Gurawara (1975), supra. Aminomethyl-1%-polymer was prepared by the method of Sparrow, J. Org. Chem. 41, 1350 (1976). Amino groups on polymers was determined by the method of Gisin, Anal. Chim. Acta. 58, 248 (1972).

[3-Nitro-4-(Boc-glycyloxymethyl)]benzamidomethyl-Polymer: Boc-Gly-NBA- Ⓟ

3-Nitro-4-bromomethylbenzoic acid (1.324 g., 5.1 mmole) in 25 ml. of CH$_2$Cl$_2$ was cooled to 0° and mixed with 4.2 ml. of 0.6 M dicyclohexylcarbodiimide in CH$_2$Cl$_2$ (2.52 mmole). The mixture was stirred for 15 minutes at 0° and then 15 minutes with warming to room temperature. The mixture was filtered (544 mg. dicyclohexylurea, 2.43 mmole), and the filtrate was added to 2.01 g. of aminomethyl-1%-polymer (1.72 mmole amine) along with 0.35 ml. of diisopropylethylamine. After stirring for 1 hour at 24°, the resin was filtered and washed with CH$_2$Cl$_2$. Drying in vacuo over P$_2$O$_5$ gave 2.52 g. of resin with a negligible amine content (0.001 mmole/g.).

A portion of the resin (1.20 g.) was reacted with 2.75 mmole of the cesium salt of Boc-glycine in 10 ml. of DMF for 17 hours at 24°. The resulting mixture was suspended in DMF, and fine particles were removed by the process of settling and decantation. The resin was filtered off and washed with DMF-H$_2$O (1:1), water, glacial acetic acid, water, and absolute ethanol: yield, 1.226 g. A sample was treated with 50% TFA in CH$_2$Cl$_2$ to remove Boc groups, and after neutralization the amine content was 0.62 mmole/g.

Synthesis of Protected Peptide [CH$_3$(CH$_2$)$_4$NH$_2$$^{31}$]-$\beta_h$-EP (IV)

A sample (612 mg., 0.375 mmole) of [3-nitro-4-Boc-glycyloxymethyl)]-benzamidomethyl-polymer (Boc-Gly-NBA-polymer) was carried through the same synthetic procedures described previously for Example 1 for assembly of the sequence corresponding to positions 1-30 of $\beta_h$-EP. The last Boc group was removed with TFA to avoid t-butylation of Met residues in HF: yield, 2.496 g.

A sample (339 mg., 51 μmole) of protected $\beta_h$-EP-(1-30)-NBA-polymer was stirred in 2.0 ml. of DMF containing 20 μl of glacial acetic acid and 0.2 ml. of n-amylamine (1.75 mmole) for 3 hours at 24°. The mixture was diluted with anhydrous ether (10 ml.), cooled to −60° and filtered: yield, 322 mg. This material was taken to the HF treatment (see below).

Synthesis of Protected Peptide Polymers of [Gly$^{31}$]-$\beta_h$-EP-Gly-NH$_2$ (V), [Gly$^{31}$]-$\beta_h$-EP-Gly-Gly-NH$_z$ (VI) and [Gln$^8$, Gly$^{31}$]-$\beta_h$-EP-Gly-Gly-NH$_z$ (VII)

Solid-phase synthesis of the appropriate sequence was performed on Boc-Gly-benzhydrylamine-1%-polymer (0.33 mmole/g.) in a Beckman Model 990 peptide synthesizer. Side-chain protection and coupling were performed as described for the synthesis of $\beta_h$-EP except that Z protection was used for the side-chain of Tyr in position 1 and a fully automated symmetrical anhydride program was employed. The last Boc group was removed with TFA.

Isolation and Characterization of Peptides IV, V, VI and VII

Protected peptide IV and protected peptide polymers V, VI and VII were treated with liquid HF. The peptides were purified by gel filtration on Sephadex G-10 and chromatography on CM-cellulose according to procedures previously described in U.S. Pat. No. 4,116,950. Final purification was effected by partition chromatography on Sephadex G-50 in either 1-butanol/HOAc/pyridine/H$_2$O (20:5:1:25) (System A) or 1-butanol/HOAc/pyridine/H$_2$O (200:50:1:250) (System B) as follows: [Gly$^{31}$]-$\beta_h$-Gly-NH$_2$, System A, R$_f$ 0.51; [CH$_3$(CH$_2$)$_4$NH$_2$$^{31}$]-$\beta_h$-EP, System B, R$_f$ 0.61; [Gly$^{31}$]-$\beta_h$-EP-Gly-Gly-NH$_2$, System A, R$_f$ 0.46; [Gln$^8$, Gly$^{31}$]-$\beta_h$-EP-Gly-Gly-NH$_2$, System A, R$_f$ 0.45. From 50 μmole of starting Boc-Gly-resin, there was obtained: IV, 48 mg.; V, 80.5 mg.; VI, 56.5 mg.; VII, 68.5 mg. The peptides were homogeneous on thin-layer chromatography (50 μg on silica gel with ninhydrin and Cl$_2$-tolidine detection) in 1-butanol/pyridine/HOAc/H$_2$O (5:5:1:4) with R$_f$ values as follows: IV, 0.75; V, 0.53; VI, 0.53; VII, 0.54. They were homogeneous on paper electrophoresis on Whatman 3MM (50 ug, 400 V, 4–6 h, ninhydrin and Cl$_2$-tolidine detection) at pH 3.7 (IV, R$_f$ 0.65; V, R$_f$ 0.65; VI, R$_f$ 0.64; VII, R$_f$ 0.65) and at pH 6.7 (IV, R$_f$ 0.60; V, R$_f$ 0.52; VI, R$_f$ 0.50; VII, R$_f$ 0.58) with R$_f$ values being relative to lysine. Amino acid analyses of 24-h acid hydrolysates were in agreement with expected values (Table 5). Since n-amylamine could not be determined on the amino acid analyzer, the hydrolysate of peptide IV was run on paper electrophoresis (Whatman 3MM) at pH 3.7 (pyridine-acetic acid buffer) for 3 hours at 400 V (ninhydrin detection). Authentic n-amylamine standards ran with mobility 1.34 times that of lysine, and the hydrolysate of IV showed an identical spot with approximately the correct intensity.

molecule by insertion of one or two glycyl residues was also determined. The first insertion to give peptide V does give a further increase in activity. Then an additional insertion to give VI gives still another increase to over four times the potency of $\beta_h$-EP. Thus, stepwise extension at the COOH-terminus is paralleled by a progressive increase in binding affinity.

The effect in going from [Gly$^{31}$]-$\beta_h$-EP to [Gly$^{31}$]-$\beta_h$-EP-NH$_2$ is the elimination of a carboxyl group, the consequence of eliminating the remaining carboxyl group in the molecule at position 8 was tested. This was implemented by taking the structure of the highly active peptide VI and formally replacing Glu-8 by a Gln residue. The resulting peptide VII exhibited an activity in the binding assay of nine times that of $\beta_h$-EP.

I claim:

1. Analogs of endorphin of the formula

TABLE 5

| Residue | Amino acid analyses of synthetic $\beta_h$-EP analogs | | | |
|---|---|---|---|---|
| | [Gly$^{31}$]-$\beta_h$-EP—Gly—NH$_2$ | [CH$_3$(CH$_2$)$_4$NH$_2$$^{31}$]-$\beta_h$-EP | [Gly$^{31}$]-$\beta_h$-EP—Gly—Gly—NH$_2$ | [Gln$^8$,Gly$^{31}$]-$\beta_h$-EP—Gly—Gly—NH$_2$ |
| Lys | 4.85 (5) | 4.95 (5) | 4.95 (5) | 4.93 (5) |
| Asp | 2.02 (2) | 2.08 (2) | 2.00 (2) | 2.05 (2) |
| Thr | 2.86 (3) | 2.73 (3) | 2.67 (3) | 2.77 (3) |
| Ser | 1.71 (2) | 1.83 (2) | 1.98 (2) | 1.84 (2) |
| Glu | 2.20 (2) | 2.04 (2) | 2.13 (2) | 2.16 (2) |
| Pro | 1.07 (1) | 1.01 (1) | 1.05 (1) | 0.85 (1) |
| Gly | 4.95 (5) | 2.97 (3) | 5.62 (6) | 6.12 (6) |
| Ala | 1.95 (2) | 1.98 (2) | 2.02 (2) | 2.16 (2) |
| Val | 1.05 (1) | 0.98 (1) | 1.02 (1) | 1.09 (1) |
| Met | 0.99 (1) | 1.03 (1) | 1.04 (1) | 0.99 (1) |
| Ile* | 1.35 (2) | 1.25 (2) | 1.50 (2) | 1.58 (2) |
| Leu | 2.03 (2) | 1.97 (2) | 2.10 (2) | 1.98 (2) |
| Tyr | 2.02 (2) | 2.08 (2) | 2.03 (2) | 1.84 (2) |
| Phe | 2.02 (2) | 2.09 (2) | 1.91 (2) | 1.67 (2) |
| CH$_3$(CH$_2$)$_4$NH$_2$** | — | 1.0 (1) | — | — |

Analyses were done on 24-h Gn HCl hydrolysates (theoretical values in parentheses).
*Low values are accounted for by the presence of the acid-resistant Ile-Ile moiety.
**Identified and estimated on paper electrophoresis (see text).

EXAMPLE 4

Bioassay for Opiate Activity

Opiate activity was measured in the rat brain binding assay in which tritiated $\beta_h$-EP is used as primary ligand (Ferrara et al., Biochem. Biophys. Res. Comm. 89, 786 [1979]).

Under these assay conditions, methionine-enkephalin has low activity (5% of $\beta_h$-EP) and that of the "non-enkephalin" segment $\beta_c$-EP-(6–31) is negligible. The activities of the analogs described herein are shown in Table 6.

TABLE 6

Relative Potency of Synthetic $\beta$-Endorphin Analogs with Extension at the COOH-Terminus by Receptor Binding Assay

| Synthetic Peptides | IC$_{50}$$^a$ | Relative Potency |
|---|---|---|
| $\beta_h$-Endorphin | 6.5 × 10$^{-10}$ | 100 |
| [CH(CH$_2$)$_4$NH$_2$$^{31}$]-$\beta_h$-EP | 3.3 × 10$^{-10}$ | 197 |
| [Gly$^{31}$]-$\beta_h$-EP—Gly—NH$_2$ | 1.9 × 10$^{-10}$ | 342 |
| [Gly$^{31}$]-$\beta_h$-EP—Gly—Gly—NH$_2$ | 1.5 × 10$^{-10}$ | 433 |
| [Gln$^8$,Gly$^{31}$]-$\beta_h$-Gly—Gly—NH$_2$ | 0.7 × 10$^{-10}$ | 929 |

$^a$50% inhibiting concentration in M

Replacement of Glu-31 by Gly caused little if any change in potency in the binding assay (Example 2). Substitution in this position by the very hydrophobic alkyl chain in n-amylamine causes a considerable increase in activity. When position 31 is occupied by a glycine amide moiety an even greater increase in activity occurred. Increasing chain length at this end of the

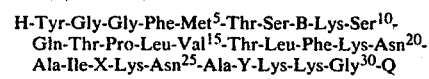

H-Tyr-Gly-Gly-Phe-Met$^5$-Thr-Ser-B-Lys-Ser$^{10}$-Gln-Thr-Pro-Leu-Val$^{15}$-Thr-Leu-Phe-Lys-Asn$^{20}$-Ala-Ile-X-Lys-Asn$^{25}$-Ala-Y-Lys-Lys-Gly$^{30}$-Q   I wherein B is Glu or Gln, X is Ile or Val; Y is His or Tyr and Q is —NH—lower alkyl or (Gly)$_n$—A where n is an integer from 1 to 5 and A is —OH or —NH$_2$ and the pharmaceutically acceptable acid addition salts thereof.

2. The compounds of claim 1 wherein X is Ile and Y is Tyr.

3. The compounds of claim 2 wherein Q is (Gly)$_n$-A.

4. The compound of claim 3 which is [Gly$^{31}$]-$\beta_h$-endorphin.

5. The compound of claim 3 which is [Gly$^{31}$]-$\beta_h$-endorphinamide.

6. The compound of claim 3 which is [Gly$^{31}$]-$\beta_h$-endorphinyl glycine.

7. The compound of claim 3 which is [Gly$^{31}$]-$\beta_h$-EP-Gly-NH$_2$.

8. The compound of claim 3 which is [Gly$^{31}$]-$\beta_h$-EP-Gly-Gly-NH$_2$.

9. The compound of claim 3 which is [Gln$^8$, Gly$^{31}$]-$\beta_h$-EP-Gly-Gly-NH$_2$.

10. The compounds of claim 2 wherein Q is —NH—lower alkyl.

11. The compound of claim 10 which is [CH$_3$(CH$_2$)$_4$—NH$_2$$^{31}$]-$\beta_h$-EP-Gly-Gly-NH$_2$.

* * * * *